United States Patent [19]

Gauthier-Lafaye et al.

[11] 4,293,718

[45] Oct. 6, 1981

[54] PREPARATION OF ACETALDEHYDE

[75] Inventors: Jean Gauthier-Lafaye, Lyons; Robert Perron, Charly, both of France

[73] Assignee: Rhone-Poulenc Industries, Paris, France

[21] Appl. No.: 87,631

[22] Filed: Oct. 23, 1979

[30] Foreign Application Priority Data

Oct. 31, 1978 [FR] France ............................. 78 31634

[51] Int. Cl.³ ............................................. C07C 45/49
[52] U.S. Cl. ................................... 568/487; 568/485; 568/485
[58] Field of Search ............... 260/604 AC, 601 R; 568/485, 487, 491

[56] References Cited

U.S. PATENT DOCUMENTS

| | | | |
|---|---|---|---|
| 3,248,432 | 4/1966 | Riley | 260/601 R |
| 3,285,948 | 11/1966 | Butter | 260/601 R |
| 3,356,734 | 12/1967 | Kuraishi et al. | 260/601 R |
| 4,151,208 | 4/1979 | Pretzer et al. | 260/601 R |

FOREIGN PATENT DOCUMENTS

| | | | |
|---|---|---|---|
| 52-133914 | 11/1977 | Japan | 568/428 |
| 52-136111 | 11/1977 | Japan | 568/428 |
| 1546428 | 5/1979 | United Kingdom | 568/882 |

*Primary Examiner*—Werren B. Lone
*Attorney, Agent, or Firm*—Burns, Doane, Swecker & Mathis

[57] ABSTRACT

Acetaldehyde is prepared by reacting methanol with a mixture comprising hydrogen and carbon monoxide, which mixture comprises at least 25 mol percent hydrogen, in the presence of cobalt, an ionic iodide and a halogen-containing promoter which is different from the ionic iodide. The reaction is best carried out at a temperature of at least 165° C. and with a ratio of gram-ions of $I^-$ originating from the ionic iodide to gram-atoms of cobalt of at least 5 and a ratio of gram-atoms of halogen from the halogen-containing promoter to gram-ions of $I^-$ in the range of about 0.001 to about 0.1

22 Claims, No Drawings

PREPARATION OF ACETALDEHYDE

CROSS-REFERENCE TO RELATED APPLICATION

Our copending application, Ser. No. 87,632 filed concurrently herewith and assigned to the assignee hereof.

BACKGROUND OF THE INVENTION

1. Field of the Invention

The present invention relates to a process for the preparation of acetaldehyde. The process comprises the carbonylation of methanol in the presence of hydrogen. In another aspect, this invention relates to a process for the preparation of acetaldehyde which comprises reacting methanol with a mixture of CO and $H_2$ in the presence of cobalt, a halogen-containing promoter and an ionic iodide.

2. Description of the Prior Art

Acetaldehyde is an intermediate of great value in the chemical industry. It is useful, in particular, for the manufacture of acetic acid and acetic anhydride, e.g., see the *Encyclopedia of Chemical Technology*, Kirk-Othmer, 3rd Edition, Volume 1, pages 97 et seq.

Industrial processes for producing acetaldehyde are well known to this art. The process which is most widely used at the present time is the direct oxidation of ethylene. Since this hydrocarbon originates from petroleum, however, it is becoming more economical to select raw materials such as methanol which originate from synthesis gas.

The use of methanol as the raw starting material in the synthesis of products which are conventionally derived from ethylene on an industrial scale has formed the subject, and continues to form the subject, of much research. This research essentially relates to the application of carbonylation techniques, i.e., the reaction of carbon monoxide with methanol, optionally in the presence of hydrogen.

Much of the earlier work was related to the homologization of methanol, i.e., the production of ethanol by the carbonylation of methanol.

It is well known that methanol reacts with a mixture of carbon monoxide and hydrogen, e.g., employed in a 1:1 ratio, in the presence of dicobalt octacarbonyl at 185° C. and under a pressure of 360 atmospheres. Under these conditions, a mixture of various products, including ethanol, is obtained with a relatively low selectivity. This reaction is discussed in Wender et al., *Science*, Volume 113, page 206 (1951).

Other authors have shown that if the homologization reaction is carried out in the presence of cobalt diacetate at 200° C. and under 200 to 350 atmospheres of pressure, the yield of ethanol can be improved by conducting the reaction in the presence of an iodine-containing promoter, e.g., $I_2$ or $CH_3I$, and a gaseous mixture which is rich in carbon monoxide. Such a reaction is discussed in Berty et al., *Chem. Tech.*, Volume 5, pages 260–266 (1956).

Other improvements in the production of ethanol have been provided by adding to the aforenoted catalyst system a phosphorous compound which is soluble in methanol, as in U.S. Pat. No. 3,248,432, by the introduction of ruthenium halides or osmium halides, as in U.S. Pat. No. 3,285,948, or by adding a tertiary phosphine and employing a hydrocarbon as a solvent, as in British Pat. No. 1,546,428.

Nevertheless, these processes cannot be applied on an industrial scale as they do not make it possible to achieve high selectivities with respect to ethanol and they consequently require the use of complex installations for separating the various constituents of the mixture obtained, which adversely affects the overall economy of such a process to an unacceptable extent.

Based upon these findings, other workers have directed their attention towards the production of acetaldehyde. U.S. Pat. No. 3,356,734 discloses that the presence of an amount of cobalt less than 2 millimols of cobalt per mol of methanol in a cobalt-halogen catalyst system favors the conversion of methanol to acetaldehyde. In fact, if the carbonylation of methanol is carried out with a $CO/H_2$ molar ratio of 1.4 for 2 hours at 185° C. under a pressure of 300 to 400 atmospheres employing the technique disclosed in U.S. Pat. No. 3,356,734, about 130 g of acetaldehyde are obtained per liter of reaction medium per hour. This is a productivity on the order of 70 g of acetaldehyde per hour per gram of cobalt employed in the reaction, taking into account the fact that the dimethoxyethane formed is a potential source of acetaldehyde.

More recent work, e.g., that described in published Japanese Patent Application Nos. 77/136,111 and 77/133,914, has shown that the results achieved with the aid of the cobalt-halogen catalyst system can be substantially improved by adding a large amount of a phosphorus, arsenic, antimony or bismuth compound to the system of cobalt and iodine. Nevertheless, the productivity of acetaldehyde relative to the cobalt employed remains too low for such processes to be of value in industry. Moreover, the known processes convert a substantial part of the methanol to butanol, butanal and butenal. These are products for which there is a variable demand and which adversely affect the overall economy of the process by necessitating additional separation steps.

SUMMARY OF THE INVENTION

Accordingly, a major object of the present invention is the provision of a novel process for the selective carbonylation of methanol, affording yields of acetaldehyde heretofore unavailable to this art, and which novel process is conspicuously devoid of those disadvantages and drawbacks which heretofore have characterized the prior art process.

It is another object of this invention to provide a more efficient and productive process for the carbonylation of methanol to produce acetaldehyde.

Another object of this invention is to provide a process for producing acetaldehyde by the carbonylation of methanol which converts little or none of the methanol to butanol, butanal, or butenal.

Another object of the present invention is to provide a process for the carbonylation of methanol in the presence of hydrogen and cobalt which considerably increases the productivity per hour of acetaldehyde relative to the amount of cobalt employed in the reaction, virtually without loss of productivity relative to the reaction volume.

It has now surprisingly been discovered that it is possible to selectively obtain acetaldehyde, possibly in the form of the corresponding dimethylacetal, by reacting methanol with a mixture of carbon monoxide and hydrogen which contains at least 25 mol% hydrogen. The reaction is best run at a temperature on the order of at least 165° C. and in the presence of cobalt, at least one ionic iodide and at least one halogen-containing promoter.

In a preferred embodiment of this invention, the ratio of the gram-ions of $I^-$, originating from the ionic iodide, to the number of gram-atoms of cobalt employed is at least 5; and, the number of gram-atoms of halogen originating from the halogen-containing promoter represent from about 0.1 to about 10% of the number of gram-ions of $I^-$.

According to a preferred embodiment of this invention, therefore, it has been surprisingly discovered that remarkable results, expressed in terms of the productivity of acetaldehyde, can be obtained by means of the combined use of the two types of "promoter" mentioned above, namely, the ionic iodide and the halogen-containing promoter, particularly when the ionic iodide is employed in an amount which is such that the ratio $(I^-/Co)$ is greater than or equal to 5 and there is a very small proportion of covalent halide.

Other objects, aspects and advantages of this invention will be apparent to those skilled in the art upon a study of this disclosure and the appended claims.

DETAILED DESCRIPTION OF THE INVENTION

More particularly, the process of this invention requires the use of at least one ionic iodide. The term "ionic iodide" is to be understood as meaning any inorganic or organic iodide, taken either alone or in admixture, the cation of which is selected from the group consisting of alkali metal cations, alkaline earth metal cations, ammonium and quaternary ammonium cations and phosphonium and quaternary phosphonium cations. The precise nature of the ammonium and phosphonium cation is not of critical importance. The choice of a suitable cation is further governed, however, by considerations of a practical nature, such as the solubility, availability and convenience of using the particular ionic iodide. In this regard, examples of suitable compounds are the quaternary ammonium iodides derived from lower trialkylamines, (e.g., trimethylamine, and tributylamine), alkylarylamines (such as dimethylaniline), cyclic tertiary amines (such as N-alkylpyrrolidines or piperidines), N-alkylhexamethyleneimines, pyrrole, pyridine or alkylpyridines which are quaternized by treatment with esters of hydriodic acid and aliphatic alcohols. Bis-quaternary ammonium iodides which are derived, for example, from tetraalkylalkylenediamines, are also within the scope of the present invention.

Examples of suitable phosphonium iodides for purposes of this invention are those derived from triarylphosphines and trialkylphosphines, preferably those which are readily available, e.g., triphenylphosphine, tritolylphosphine, trixylylphosphine, trimethylphosphine, tributylphosphine and tricyclohexylphosphine, which are quaternized by alkyl or aralkyl iodides. Bis-quaternary phosphonium iodides derived, for example, from bis-$\alpha,\omega$-(diphenylphosphino)alkanes, are also suitable for purposes of the present invention.

A preferred embodiment of the present invention comprises the use of alkali metal or alkaline earth metal iodides, e.g., LiI, NaI, KI, CsI and $CaI_2$. The use of one or more alkali metal iodide is preferred with the use of NaI or KI being most preferred.

The ratio of gram-ions of $I^-$ to gram-atoms of Co $(I^-/Co)$, with $I^-$ originating from the ionic iodide, is preferably equal to at least 5. Although this ratio can vary within wide limits, it does not seem to be advantageous to exceed a value of 200. In a specific embodiment of this invention, the ratio $(I^-/Co)$ is greater than or equal to 10. It is particularly advantageous for the ratio $I^-/Co$ to be greater than or equal to 20.

The process according to the present invention also requires the use of at least one halogen-containing promoter. The term "halogen-containing promoter" is to be understood as meaning any compound formed by replacing at least one hydrogen atom of an organic molecule which only contains carbon and hydrogen with a halogen, e.g., hydrocarbyl chlorides, bromides, and most preferably iodides, or, any compound which, under the reaction conditions, is capable of leading to the production of a methyl halide in the reaction medium, in particular; $Cl_2$, $Br_2$, $I_2$, HCl, HBr, HI, $CoBr_2$ and $CoI_2$.

For purposes of this invention it is preferred to use the lower alkyl chlorides, bromides and iodides having from 1 to 4 carbon atoms in the molecule. Examples are methyl bromide and iodide and ethyl bromide and iodide. The use of methyl iodide or of one of its progenitors, e.g., iodine, hydriodic acid and cobalt iodide, is most preferred.

The effect provided by the halogen-containing promoter is appreciable, even in minor proportions, e.g., proportions on the order of 0.1 gram-atom of halogen (denoted as "X" in the description which follows) per 100 gram-ions of iodide, i.e., a ratio of $X/I^-$ on the order of 0.001. It is not desirable to exceed a value of 0.1 for this ratio, however, particularly to limit the corrosion of the apparatus, but also for technological reasons. The process is preferably carried out with a ratio of $X/I^-$ in the range of about 0.01 to about 0.08.

The process according to this invention is also carried out in the presence of cobalt. Any source of cobalt which will react with carbon monoxide in the reaction medium to provide a cobalt carbonyl, cobalt carbonyl hydride or a cobalt carbonylate complex can be used for purposes of the present invention.

Typical sources of cobalt are, for example, finely divided cobalt metal, inorganic salts such as cobalt carbonate and organic salts, in particular, fatty acid salts. Cobalt carbonyls and cobalt carbonyl hydrides, or, the complexes thereof, can also be employed. Cobalt acetate, cobalt formate, cobalt halides, particularly cobalt iodide, and dicobalt octacarbonyl are among the cobalt derivatives which are suitable for carrying out the process of the present invention.

The process is carried out with a catalytically effective amount of cobalt. An effective amount of cobalt is that quantity sufficient to obtain the reaction rate and results desired. In general, an effective amount is such an amount that the ratio of the number of milligram-atoms of cobalt to the number of mols of methanol $(Co/CH_3OH)$ is in the range of about 0.01 to about 1 and preferably in the range of about 0.05 to 0.4.

The carbonylation process according to the present invention is preferably carried out in the liquid phase. Since it is preferred to carry out the process with excess methanol, the simultaneous use of an additional solvent is generally superfluous, but, in principle, such inert organic solvents as hydrocarbons, esters, ethers and the reaction products, can be used.

It is not necessary to initially purify or dehydrate the methanol employed as technical-grade methanol can be used. The methanol used can contain up to 50% water and/or methyl acetate. Similarly, the halogen-containing promoters, the ionic iodides and the cobalt-based compounds used can also be of technical grade.

In accordance with the present invention, a mixture of carbon monoxide and hydrogen is reacted with methanol. It is essential that the mixture contain at least 25 mol% hydrogen. In general, mixtures containing up to 95% hydrogen can be used. The use of mixtures containing from 40 to 80% of hydrogen are preferred. The mixture of gases can contain impurities such as carbon dioxide, oxygen, methane and nitrogen.

Although the particular pressure at which the reaction is conducted is not critical, the reaction is generally run with a total pressure in the range of about 50 to about 600 bars. The total pressure is preferably between 75 and 350 bars and most preferably between 100 and 320 bars.

It is preferred that the reaction temperature employed be at least about 165° C. The temperature can reach 240° C. if the reaction is conducted without a solvent. If a solvent is employed, this being optional within the scope of the present invention, the temperature can be as high as about 300° C. The reaction temperature preferably is within the range of about 180° C. to about 230° C.

In order to further illustrate the present invention and the advantages thereof, the following specific examples are given, it being understood that some are intended only as illustrative and in nowise limitative.

The conventions used in the examples below are as follows:

AcH denotes acetaldehyde.
AcOMe denotes methyl acetate.
AcOH denotes acetic acid.
EtOH denotes ethanol.
$C_4$ denotes all the products formed which have 4 carbon atoms in the molecule, particularly butenal, butanal and butanol.
MeOMe denotes dimethyl ether (which product can be recycled to the reaction).
RR, for a given product, is equal to the ratio of the number of mols of the product formed during the reaction to the number of mols of methanol employed in the reaction. Exceptions are RR($C_4$) and RR (MeOMe), which are equal to twice the ratio defined above.
$\Sigma RR$ is the sum of the RR values defined above for all the products with the exception of dimethyl ether.
N.B. In all the examples below, $$\frac{RR(EtOH)}{\Sigma RR}$$

is less than 0.01.

CONTROL EXPERIMENTS (a to e)

A first series of control experiments (a, b and c) was carried out in accordance with the analogous procedure described below for control experiment b.

50 ml (1,229 mmols) of methanol, 0.042 g (0.29 mmol) of methyl iodide and 0.010 g (0.058 mg-atom) of dicobalt octacarbonyl were introduced into a Z8-CNDT 17-12 (AFNOR Standard Specification) stainless steel autoclave having a capacity of 125 ml.

After closing the autoclave, a pressure of 180 bars was established with the aid of a 1/1 mixture of CO and $H_2$. Agitation by means of a reciprocating system was started and the autoclave was heated to 200° C. over the course of about 25 minutes by means of an annular furnace. The total pressure in the autoclave was then 250 bars and it was maintained between 240 and 254 bars by periodically re-introducing the CO/$H_2$ mixture. After a reaction time of 2 hours at the temperature indicated (total absorption of 56 bars of the CO/$H_2$ mixture), the heating and the agitation were stopped. The autoclave was cooled and degassed. The resulting reaction mixture was analyzed by gas chromatography after having been diluted with water and acidified with 36 N sulphuric acid.

The particular conditions and results obtained for control runs a, b and c are shown in Table I below.

A second series of control experiments, runs d and e, was carried out in accordance with the analogous procedure described below for control experiment d.

100 ml (2,437 mmols) of methanol, 2 g (12 mmols) of potassium iodide and 0.020 g (0.117 mg-atom) of dicobalt octacarbonyl were introduced into a Z 8-CNDT 17-12 (AFNOR Standard Specification) stainless steel autoclave having a capacity of 250 ml.

After closing the autoclave, a pressure of 140 bars was established with the aid of a 1/1 mixture of CO and $H_2$.

Agitation by means of a conventional reciprocating system was started and the autoclave was heated to 200° C. by means of an annular furnace. The total pressure in the autoclave was then 255 bars. This pressure was maintained between 248 and 255 bars by periodically re-introducing the CO/$H_2$ mixture. After a reaction time of 90 minutes at the temperature indicated (total absorption of 42 bars of the CO/$H_2$ mixture), the heating and the agitation were stopped. The autoclave was then cooled and degassed. The resulting reaction mixture was then analyzed as before.

The particular conditions employed and results obtained for runs d and e are also shown in Table I below.

TABLE I

CONTROL EXPERIMENTS

| CONTROL | Co/CH$_3$OH | IONIC IODIDE Nature | I$^-$/Co | HALOGEN-CONTAINING PROMOTER Nature | X/Co | $\Sigma RR$ | $\frac{RR}{\Sigma RR}$ (%) | AcH Productivity g/hour × liters | g/hour × Co* | MeOMe RR % | BY PRODUCTS $\frac{RR}{\Sigma RR}$ (%) | |
|---|---|---|---|---|---|---|---|---|---|---|---|---|
| | | | | | | | | | | | C$_4$ | AcOH + AcOMe |
| a(++) | 0.047 | — | 0 | — | 0 | 0 | — | 0 | 0 | 0 | — | — |
| b | 0.047 | — | 0 | CH$_3$I | 5 | 6 | 94 | 30 | 440 | 5.1 | — | 6 |
| c | 0.047 | — | 0 | CH$_3$I | 100 | 9.4 | 94 | 47 | 680 | ≧16 | 0 | 6 |
| d | 0.048 | KI | 102 | — | 0 | 4.2 | 92.5 | 28.0 | 405 | 0.7 | 2 | 5.5 |

TABLE I-continued

CONTROL EXPERIMENTS

| CONTROL | Co/CH$_3$OH | IONIC IODIDE Nature | I$^-$/Co | HALOGEN-CONTAINING PROMOTER Nature | X/Co | ΣRR | $\frac{RR}{\Sigma RR}$ (%) | AcH Productivity g/hour × liters | g/hour × Co* | MeOMe RR % | BY PRODUCTS $\frac{RR}{\Sigma RR}$ (%) AcOH + C$_4$ AcOMe |
|---|---|---|---|---|---|---|---|---|---|---|---|---|
| e | 0.049 | (1) | 97 | — | 0 | 5.6 | 91 | 36.6 | 531 | 0.9 | — | 9 |

(++)Experiment carried out under a total pressure of 270 bars.
(1)= [(CH$_3$) (C$_4$H$_9$)$_3$P] I.
*Productivity expressed in grams of AcH formed per gram of cobalt employed and per hour.

EXAMPLES 1 TO 10

These examples illustrate the use of various ionic iodides.

A procedure analogous to that described above for control experiment (d) was used.

The common conditions for Examples 1 to 10 were as follows:
CO/H$_2$ mixture=1:1
Temperature of about 200° C.
Total pressure: 250 bars
Source of cobalt: Co$_2$(CO)$_8$
Co/CH$_3$OH between 0.045 and 0.05, unless otherwise indicated
Halogen-containing promoter: CH$_3$I The particular conditions employed and the results obtained are shown in Table II below.

EXAMPLES 11 TO 13

These examples illustrate the use of various halogen-containing promoters for the process of the present invention.

The process was carried out as in control experiment (b) described above.

The common conditions for Examples 11 to 13 were as follows:
CO/H$_2$ mixture containing 50% (in mols) of H$_2$
Temperature: 200° C.
Total pressure: 250 bars
Reaction time: 40 minutes
Source of cobalt: Co$_2$(CO)$_8$, Co/CH$_3$OH=0.144
Ionic iodide: KI, I$^-$/Co=34
Halogen-containing promoter: X/I$^-$=5.8%

The particular conditions and also the results obtained are shown in Table III below:

TABLE II

EXAMPLES 1 to 10

| EXAMPLE No. | IONIC IODIDE Nature | I$^-$/Co | X/I$^-$ in % | TIME in minutes | ΣRR in % | RR/ΣRR % | AcH Productivity g/hour × liters | g/hour × Co (*) | MeOMe RR in % | C$_4$ RR/ΣRR (in %) |
|---|---|---|---|---|---|---|---|---|---|---|
| 1 | NaI | 107 | 4.9 | 90 | 20.8 | 85 | 126 | 1,900 | 3.3 | 3 |
| 2 | KI | 102 | 4.8 | 90 | 17.6 | 87 | 109 | 1,560 | 3 | 1.6 |
| 3 | LiI | 102 | 4.8 | 90 | 19.7 | 84 | 118 | 1,710 | 2.7 | 3.9 |
| 4 | CsI | 102 | 4.8 | 90 | 15.6 | 87 | 97 | 1,370 | 3.2 | 1.9 |
| 5$^{(a)}$ | CaI$_2$ | 93 | 5.9 | 40 | 13.6 | 69 | 150 | 710 | 1.3 | 21.5 |
| 6 | NH$_4$I | 102 | 2.5 | 30 | 4.2 | 84 | 75 | 1,100 | 3.6 | — |
| 7 | [(CH$_3$)(n-C$_4$H$_9$)$_3$N] I | 97 | 2.5 | 45 | 10.1 | 90 | 130 | 1,830 | 1.4 | — |
| 8 | [(CH$_3$)(n-C$_4$H$_9$)$_3$P] I | 99 | 5.0 | 90 | 18.9 | 85 | 114 | 1,650 | 4 | 2.0 |
| 9$^{(b)}$ | [(CH$_3$)(C$_6$H$_{11}$)$_3$P] I | 95 | 2.5 | 45 | 12.1 | 86 | 148 | 2,040 | 1.7 | — |
| 10 | [(CH$_3$)(C$_6$H$_5$)$_3$P] I | 95 | 2.5 | 45 | 12.2 | 86 | 150 | 2,060 | 1.6 | — |

(a)experiment carried out with Co/CH$_3$OH = 0.148
(b)C$_6$H$_{11}$ denotes a cyclohexyl radical
(*)same comment as in Table I.

tained are shown in Table III below:

TABLE III

EXAMPLES 11 to 13

| EXAMPLE | HALOGEN-CONTAINING PROMOTER | ΣRR in % | $\frac{RR}{\Sigma RR}$ in % | AcH Productivity g/hour × liters | g/hour × Co (*) | MeOMe RR in % |
|---|---|---|---|---|---|---|
| 11 | C$_2$H$_5$Br | 15.1 | 91 | 225 | 1,090 | 1.3 |
| 12 | C$_2$H$_5$I | 15.8 | 91 | 230 | 1,110 | 1.2 |
| 13 | CH$_3$I | 16.3 | 90 | 240 | 1,160 | 1.4 |

N.B. the appearance of C$_4$ is not observed in these experiments
(*)Same as in previous tables.

EXAMPLES 14 to 17

The examples below illustrate the use of various total pressures in the process of the present invention.

The process is carried out as described for control experiment (b).

The common conditions for Examples 14 to 17 were as follows:
Temperature = 200° C.
Reaction time = 40 minutes
Source of cobalt: $Co_2(CO)_8$, $Co/CH_3OH = 0.047$
Ionic iodide: KI, $I^-/Co = 207$
Halogen-containing promoter: $CH_3I$, $X/I^- = 2.8\%$ The particular conditions and also the results obtained are shown in Table IV below:

TABLE IV

EXAMPLES 14 to 17

| EXAMPLE | TOTAL PRESSURE (BARS) | $H_2$ in mol % | $\Sigma RR$ (%) | $\frac{RR}{\Sigma RR}$ (%) | AcH Productivity g/liter × hour | AcH Productivity g/hour × Co (*) | MeOMe RR % | $\frac{RR}{\Sigma RR}$ | $C_4$ (%) |
|---|---|---|---|---|---|---|---|---|---|
| 14 | 300 | 44.5 | 10 | 89 | 144 | 2,080 | 1.6 | — | |
| 15 | 250 | 47 | 9.2 | 89 | 130 | 1,890 | 1.6 | — | |
| 16 | 225 | 54 | 7.3 | 92 | 109 | 1,580 | 1.6 | — | |
| 17 | 300 | 56 | 9.6 | 93 | 146 | 2,100 | 1.8 | — | |

N.B. No $C_4$ are observed in this series of experiments
(*)Compare preceding tables.

EXAMPLE 18

Repeating the procedure of control experiment (d), 1.22 mols of methanol, 50 ml of tetraglyme, 0.35 milligram-atom of cobalt in the form of $CoI_2$, 12 millimols of KI and 0.70 millimol of $CH_3I$ were introduced into the autoclave. The reaction temperature, reached in 20 minutes, was 200° C. with a total pressure of 250 bars, the proportion of hydrogen in the gaseous mixture was 50% (in mols). After 90 minutes, 390 g of acetaldehyde were obtained per hour per gram of cobalt with a selectivity ($RR/\Sigma RR$) of 83%.

$\Sigma RR$ was equal to 27.4% and only a small amount of $C_4$ was observed ($RR/\Sigma RR = 6\%$).

EXAMPLE 19

Repeating the procedure of control experiment (d), 2.44 mols of methanol, 0.35 milligram-atom of cobalt in the form of $Co_2(CO)_8$, 12 millimols of KI and 0.70 millimol of $CH_3I$ were introduced into the autoclave. The reaction temperature, reached in 20 minutes, was 200° C. with a total pressure of 250 bars, the proportion of hydrogen in the gaseous mixture was 50% (in mols). After 40 minutes, 1,280 g of acetaldehyde were obtained per hour per gram of cobalt with a selectivity of 87%.

$\Sigma RR$ was equal to 19% and virtually no $C_4$ was observed ($RR/\Sigma RR \leq 1\%$).

EXAMPLE 20

Repeating the procedure of control experiment (d), 2.44 mols of methanol, 0.181 milligram-atom of cobalt in the form of $Co_2(CO)_8$, 12 millimols of KI and 0.7 millimol of $CH_3I$ were introduced into the autoclave. The reaction temperature, reached in 20 minutes, was 200° C. with a total pressure of 260 bars, the proportion of hydrogen in the gaseous mixture was 60 and then 50% (in mols). After 40 minutes, 2,090 g of acetaldehyde were obtained per hour per gram of cobalt with a selectivity of 91.5%.

$\Sigma RR$ was equal to 15.2% and virtually no $C_4$ was observed.

EXAMPLES 21

Repeating the procedure of control experiment (d), 2.44 mols of methanol, 0.118 milligram-atom of cobalt in the form of $Co_2(CO)_8$, 12 millimols of KI and 0.23 millimol of $CH_3I$ were introduced into the autoclave. The reaction temperature, reached in 20 minutes, was 200° C. with a total pressure is 250 bars, the proportion of hydrogen in the gaseous mixture was 50% (in mols). After 90 minutes, 1,350 g of acetaldehyde were obtained per hour per gram of cobalt with a selectivity of 90%.

$\Sigma RR$ was equal to 14.5% and virtually no $C_4$ was observed.

EXAMPLES 22

Repeating the procedure of control experiment (d), 2.44 mols of methanol, 0.35 milligram-atom of cobalt in the form of $CoI_2$, 11.3 millimols of KI and 0.7 millimol of $CH_3I$ were introduced into the autoclave. The reaction temperature, reached in 20 minutes, was 200° C. with a total pressure of 265 bars, the proportion of hydrogen in the gaseous mixture was 50 mol%. In the course of a reaction time of 40 minutes, 1,260 g of acetaldehyde were obtained per hour per gram of cobalt, with a selectivity of 87%.

$\Sigma RR$ was equal to 18.6% and virtually no $C_4$ was observed.

EXAMPLE 23

Repeating the procedure of control experiment (d), 2.44 mols of methanol, 0.136 milligram-atom of cobalt in the form of $Co_2(CO)_8$, 12 millimols of KI and 0.70 millimol of $CH_3I$ were introduced into the autoclave. The reaction temperature, reached in 20 minutes, was 200° C. with a total pressure of 200 bars, the proportion of hydrogen in the gaseous mixture was 45% and then 50% (in mols). After 40 minutes, 1,980 g of acetaldehyde were obtained per hour and per gram of cobalt, with a selectivity of 91%. $\Sigma RR$ was equal to 10.9% and virtually no $C_4$ was observed.

EXAMPLE 24

Repeating the procedure of control experiment (b), 1.233 mols of methanol, 0.117 milligram-atom of cobalt in the form of $Co_2(CO)_8$, 12 millimols of KI and 0.23 millimol of $CH_3I$ were introduced into the autoclave. The reaction temperature, reached in 20 minutes, was 200° C. with a total pressure of 250 bars, the proportion of hydrogen in the gaseous mixture was 50 mol%. After 40 minutes, 1,300 g of acetaldehyde were obtained per hour per gram of cobalt with a selectivity of 89.5%.

ΣRR was equal to 12.3% and virtually no C$_4$ was observed.

EXAMPLE 25

Repeating the procedure of control experiment (b), 1.25 mols of methanol, 0.175 milligram-atom of cobalt in the form of Co$_2$(CO)$_8$, 6 millimols of KI and 0.34 millimol of CH$_3$I were introduced into the autoclave. The reaction temperature, reached in 20 minutes, was 160° C. with a total pressure of 250 bars, the proportion of hydrogen in the gaseous mixture was 50% (in mols). After 40 minutes, 450 g of acetaldehyde were obtained per hour per gram of cobalt with a selectivity of 83%.

ΣRR was equal to 6.9% and virtually no C$_4$ was observed.

EXAMPLE 26

Repeating the procedure of control experiment (d), 2.44 mols of methanol, 0.38 milligram-atom of cobalt in the form of CoCO$_3$, 12 millimols of KI and 0.7 millimol of CH$_3$I were introduced into the autoclave. The reaction temperature, reached in 20 minutes, was 200° C. with a total pressure of 250 bars, the proportion of hydrogen in the gaseous mixture was 50 mol%. After 40 minutes, 1,110 g of acetaldehyde were obtained per hour per gram of cobalt with a selectivity of 88%.

ΣRR was equal to 16.7% and virtually no C$_4$ was observed.

EXAMPLE 27

Repeating the procedure of control experiment (d), 2.44 mols of methanol, 0.117 milligram-atom of cobalt in the form of Co$_2$(CO)$_8$, 11.6 millimols of [(CH$_3$)(n-C$_4$H$_9$)$_3$P]I and 0.116 millimol of CH$_3$I were introduced to the autoclave. The reaction temperature, reached in 20 minutes, was 200° C. with a total pressure of 250 bars, the proportion of hydrogen in the gaseous mixture was 50% (in mols). After 90 minutes, 880 g of acetaldehyde were obtained per hour per gram of cobalt with a selectivity of 91%.

ΣRR was equal to 9.4% and virtually no C$_4$ was observed.

EXAMPLE 28

Repeating the procedure of control experiment (b), 1.24 mols of methanol, 0.175 milligram-atom of cobalt in the form of Co$_2$(CO)$_8$, 6 millimols of KI and 0.34 millimol of CH$_3$I were introduced into the autoclave. The reaction temperature, reached in 20 minutes, was 180° C. with a total pressure of 250 bars, the proportion of hydrogen in the gaseous mixture was 50 mol%. After 40 minutes, 860 g of acetaldehyde were obtained per hour per gram of cobalt with a selectivity of 87%.

ΣRR was equal to 12.7% and virtually no C$_4$ was observed.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a process for the preparation of acetaldehyde by carbonylation of methanol, the improvement which comprises (i) carbonylating methanol with a gaseous admixture of hydrogen and carbon monoxide, (ii) with the hydrogen comprising at least 25 mol percent of said admixture, and in the presence of (iii) a catalytic amount of a catalyst system comprising (iiia) cobalt, (iiib) an iodide selected from the group consisting of alkali metal iodides, alkaline earth metal iodides, ammonium iodides, quaternary ammonium iodides, phosphonium iodides and quaternary phosphonium iodides, and (iiic) a halogen-containing promoter differing from said iodide (iiib), said halogen-containing promoter being a compound formed by replacing at least one hydrogen atom of an organic molecule which only contains carbon and hydrogen with a halogen or being a compound which, under the reaction conditions, is capable of leading to the production of a methyl halide in the reaction medium and which is selected from the group consisting of Cl$_2$, Br$_2$, I$_2$, HCl, HBr, HI, CoBr$_2$ and CoI$_2$.

2. The process of claim 1 wherein the ratio of gram-ions of I$^-$ originating from the iodide (iiib) to the gram-atoms of cobalt (iiia) employed is at least 5.

3. The process of claim 1 wherein the ratio of gram-atoms of halogen originating from the halogen-containing promoter (iiic) to the gram-ions of I$^-$ originating from the iodide (iiib) is in the range of about 0.001 to about 0.1.

4. The process of claim 1 wherein the reaction temperature is at least 165° C.

5. In a process for the preparation of acetaldehyde by carbonylation of methanol, the improvement which comprises (i) carbonylating methanol with a gaseous admixture of hydrogen and carbon monoxide, (ii) with the hydrogen comprising at least 25 mol percent of said admixture, and in the presence of (iii) a catalytic amount of a catalyst system comprising (iiia) cobalt, (iiib) an iodide selected from the group consisting of alkali metal iodides, alkaline earth metal iodides, ammonium iodides, quaternary ammonium iodides, phosphonium iodides and quaternary phosphonium iodides, and (iiic) a halogen-containing promoter differing from said iodide (iiib), said halogen-containing promoter being a compound formed by replacing at least one hydrogen atom of an organic molecule which only contains carbon and hydrogen with a halogen or being a compound which, under the reaction conditions, is capable of leading to the production of a methyl halide in the reaction medium and which is selected from the group consisting of Cl$_2$, Br$_2$, I$_2$, HCl, HBr, HI, CoBr$_2$ and CoI$_2$, at (iv) a temperature of at least 165° C., wherein (v) the ratio of gram-atoms of halogen originating from the halogen-containing promoter (iiic) to the gram-ions of I$^-$ originating from the iodide (iiib) is in the range of about 0.001 to about 0.1, and (vi) the ratio of gram-ions of I$^-$ originating from the iodide (iiib) to the gram-atoms of cobalt (iiia) employed is at least 5.

6. The process of claim 1 or 5 wherein the process is carried out in the liquid phase.

7. The process of claim 1 or 5 wherein the proportion of hydrogen in the admixture is in the range of about 40 mol percent to about 80 mol percent.

8. The process of claim 2 or 5 wherein the ratio of gram-ions of I$^-$ originating from the iodide (iiib) to gram-atoms of cobalt (iiia) is at least 10.

9. The process of claim 8 wherein the ratio of gram-ions of I$^-$ originating from the iodide (iiib) to gram-atoms of cobalt (iiia) is in the range of about 20 to about 200.

10. The process of claim 3 or 5 wherein the ratio of gram-atoms of halogen originating from the halogen-containing promoter (iiic) to gram-ions of I$^-$ originating from the iodide (iiib) is in the range of about 0.01 to about 0.08.

11. The process of claim 1 or 5 wherein the iodide (iiib) is selected from the group consisting of alkali metal iodides and alkaline earth metal iodides.

12. The process of claim 11 wherein the iodide is selected from the group consisting of LiI, NaI, KI, CsI and $CaI_2$.

13. The process of claim 11 wherein the iodide is selected from the group consisting of NaI and KI.

14. The process of claim 1 or 5 wherein the halogen-containing promoter (iiic) is selected from the group consisting of the lower alkyl chlorides, bromides and iodides having from 1 to about 4 carbon atoms per molecule, $Cl_2$, $Br_2$, $I_2$, HCl, HBr, HI, $CoBr_2$, and $CoI_2$.

15. The process of claim 14 wherein the halogen-containing promoter is selected from the group consisting of methyl iodide, $I_2$, HI, and $CoI_2$.

16. The process of claim 1 or 5 wherein the amount of cobalt (iiia) employed is in the range of about 0.01 to about 1 milligram-atom of cobalt per mol of methanol.

17. The process of claim 16 wherein the amount of cobalt employed is in the range of about 0.05 to about 0.4 milligram-atom per mol of methanol.

18. The process of claim 4 or 5 wherein the reaction temperature is in the range of about 180° to about 230° C.

19. The process of claim 1 or 5 wherein the total pressure in the system is in the range of about 50 to about 600 bars.

20. The process of claim 19 wherein the total pressure is in the range of about 75 to about 350 bars.

21. The process of claim 19 wherein the total pressure is in the range of about 100 to about 320 bars.

22. A process for the preparation of acetaldehyde which comprises carbonylating methanol in the liquid phase with a gaseous admixture of hydrogen and carbon monoxide with the hydrogen comprising at least 25 mol percent of the admixture, at a temperature in the range of about 180°–230° C. and under a total pressure in the range of about 75–350 bars, and in the presence of a catalyst system comprising (i) cobalt, which is employed in an amount in the range of about 0.01 to about 1 milligram-atom of cobalt per mol of methanol, (ii) an alkali metal iodide and (iii) methyl iodide, wherein the ratio of gram-ions of $I^-$ originating from the alkali metal iodide (ii) to gram-atoms of cobalt (i) is in the range of about 20 to 200 and the ratio of gram-molecules of $CH_3I$ (iii) to gram-ions of $I^-$ originating from the alkali metal iodide (ii) is in the range of about 0.01 to 0.08.

* * * * *